(12) United States Patent     (10) Patent No.:   US 12,691,371 B1

Badyal                 (45) Date of Patent:     Jul. 28, 2026

(54) METHOD AND APPARATUS TO TEST A USER'S ABILITY AND SKILLS TO BALANCE A LEVER ON AN APEX

(71) Applicant: Surinder Badyal, Ridgecrest, CA (US)

(72) Inventor: Surinder Badyal, Ridgecrest, CA (US)

( * ) Notice: Subject to any disclaimer, the term of this patent is extended or adjusted under 35 U.S.C. 154(b) by 676 days.

(21) Appl. No.: 17/993,466

(22) Filed: Nov. 23, 2022

Related U.S. Application Data

(60) Provisional application No. 63/282,687, filed on Nov. 24, 2021.

(51) Int. Cl.
| | |
|---|---|
| *A63F 9/26* | (2006.01) |
| *A61B 5/11* | (2006.01) |
| *A63H 33/06* | (2006.01) |

(52) U.S. Cl.
CPC .............. *A63F 9/26* (2013.01); *A63H 33/06* (2013.01); *A61B 5/1124* (2013.01)

(58) Field of Classification Search
CPC .......... A63F 9/26; A63H 33/06; A61B 5/1124
USPC ......................................................... 434/29
See application file for complete search history.

(56) References Cited

U.S. PATENT DOCUMENTS

| | | | | |
|---|---|---|---|---|
| 5,240,260 A | * | 8/1993 | Strongin ................... | A63F 9/26 |
| | | | | 446/175 |
| 8,037,778 B2 | * | 10/2011 | Kazushi ................. | G05G 9/047 |
| | | | | 74/471 XY |
| 2008/0264728 A1 | * | 10/2008 | Kamiya ................. | G05G 9/047 |
| | | | | 187/222 |

* cited by examiner

*Primary Examiner* — Pierre E Elisca

(57)            ABSTRACT

A toy, game, or tool configured to test a user's ability to balance an object on an apex. The toy/game/tool is comprised of an apparatus and a lever. The apparatus is comprised substantially of a pyramidal assembly, where the pyramidal assembly further has a base, a middle section and an apex. In various embodiments, the shape of the base can be comprised of a triangle, a rectangle, circle, oval, etc. The lever has a length, a weight, and a tapered notch coupled perpendicular to an end thereon, wherein the tapered notch has a length and weight. In use, a user places the lever on a top section of the apex. The lever is rockably coupled to the apex until firmly and securely balanced thereon which can optionally be done under a timed condition.

14 Claims, 12 Drawing Sheets

30

40

600

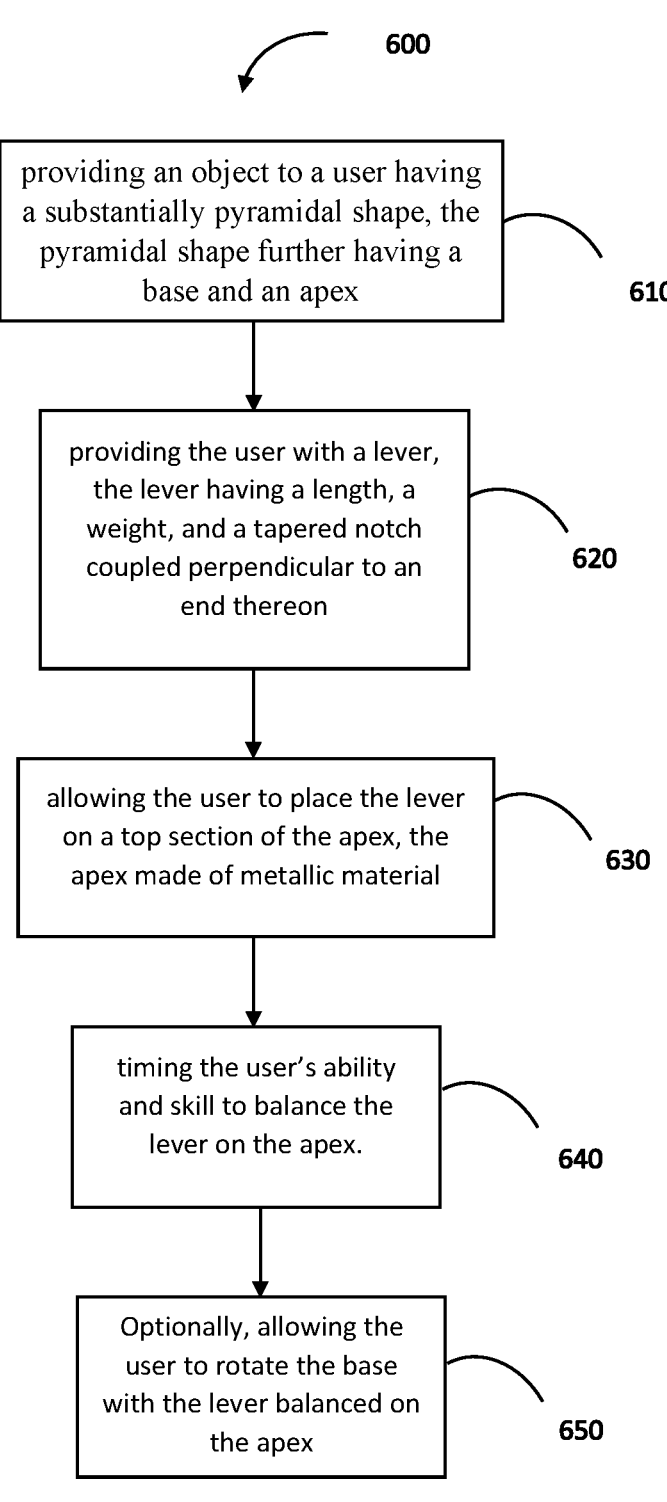

providing an object to a user having a substantially pyramidal shape, the pyramidal shape further having a base and an apex

610 providing the user with a lever, the lever having a length, a weight, and a tapered notch coupled perpendicular to an end thereon

620 allowing the user to place the lever on a top section of the apex, the apex made of metallic material

630 timing the user's ability and skill to balance the lever on the apex.

640

Optionally, allowing the user to rotate the base with the lever balanced on the apex

METHOD AND APPARATUS TO TEST A USER'S ABILITY AND SKILLS TO BALANCE A LEVER ON AN APEX

PRIORITY CLAIM

This application claims the benefit of priority under 35 U.S.C. § 119 (e) to U.S. Provisional Application No. 63/282,687, entitled "Apparatus and Method and Apparatus to Test a User's Ability and Skills to Balance a Lever on an Apex", filed Nov. 24, 2021, the entire contents of which are incorporated herein by reference.

TECHNICAL FIELD

The present invention relates generally to an apparatus and method, namely a toy and/or game, and/or tool, to test the patience, coordination, concentration, and critical thinking skills of a user to skillfully balance a lever on an apex.

BACKGROUND OF THE INVENTION

A multitude of toys, tools, and games have been introduced over the years that test various skills of a user. After considerable research and experimentation, the balancing game of the present invention has been devised to provide a user with another form of entertainment.

In light of the shortcomings in the prior art, there is definitely a need for another toy and/or game and/or tool that challenges a user's patience, coordination, concentration and critical thinking skills, while providing hours of entertainment and mental stimulation.

SUMMARY OF THE INVENTION

The present invention relates to an apparatus and method for testing a user's patience, coordination, concentration, and critical thinking skills to balance a lever on an apex.

Another aspect of the present invention is to provide a toy and/or game and/or tool for adults and children that has two main components: a pyramid-like assembly and a lever.

An additional aspect of the present invention is to provide a toy/game/tool that allows a user to balance the lever on an apex in the shortest time possible.

A further aspect of the present invention is to provide a toy/game/tool which is easy to manufacture and is also susceptible of a low cost of manufacture with regard to both materials and labor, and which accordingly is then susceptible of low prices of sale to the consuming public, thereby making such toy/game/tool economically available to the buying public.

Still yet a further feature of the present invention is to provide a game that could also be advantageously used as a tool to decide if a person would be suitable for employment in a wide range of fields as the present invention tests motivation, patience, and coordination.

Consequently, for a better understanding of the present invention, its functional advantages and the specific objects attained by its uses, reference should be made to the accompanying drawings, claims and descriptive matter in which there are illustrated preferred embodiments of the present invention.

BRIEF DESCRIPTION OF THE DRAWINGS

FIG. 6 represents an execution diagram directed to the method of testing a user's ability to balance a lever on an apex.

DETAILED DESCRIPTION OF THE INVENTION

Introduction

The following detailed description is of the best currently contemplated modes of carrying out various embodiments of the invention. The description is not to be taken in a limiting sense but is made for at least the purpose of illustrating the general principles of the invention, since the scope of the invention is best defined by the appended claims.

DETAILED DESCRIPTION

Figure 1A:
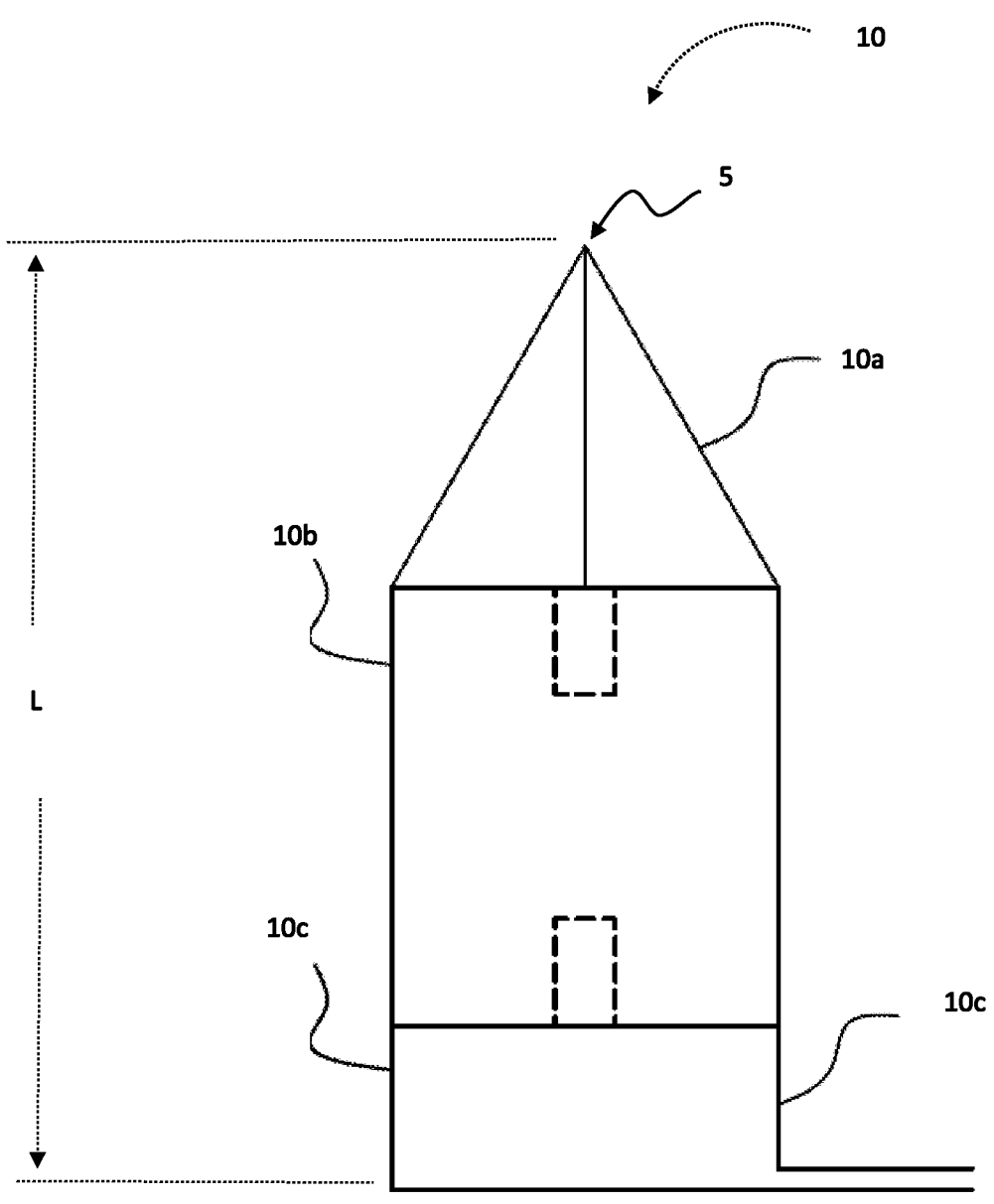
FIG. 1A shows a front perspective view of the present invention.
Figure 5:
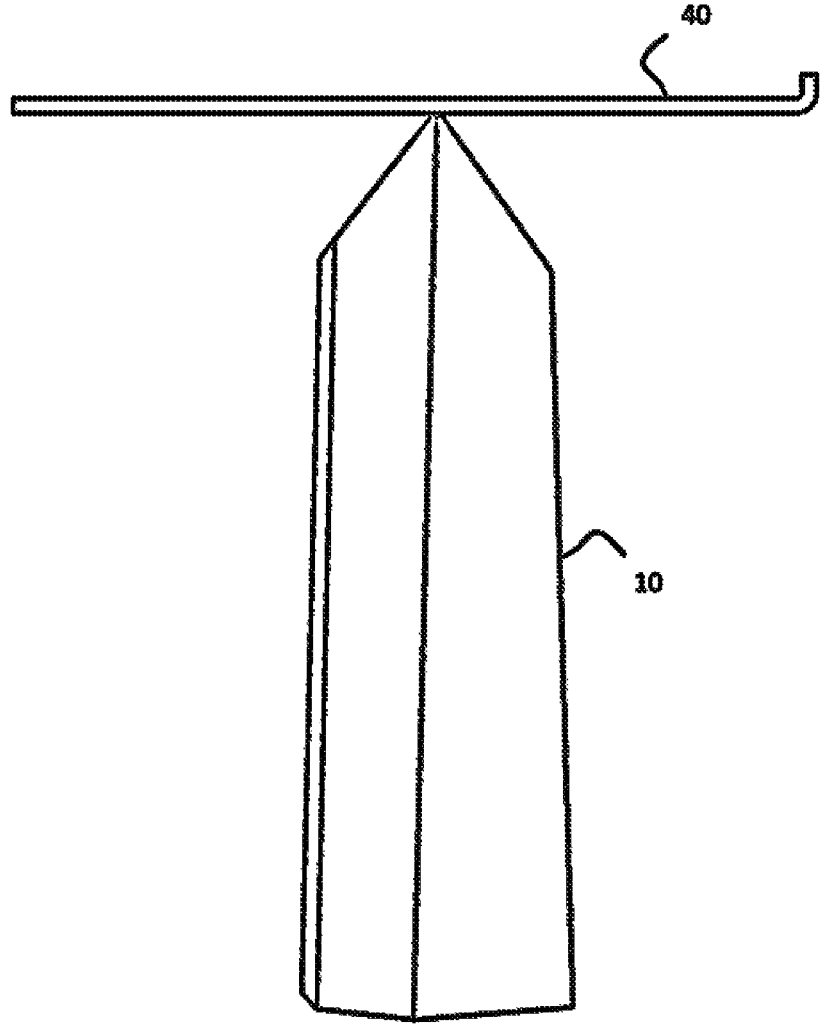
FIG. 5 is another front perspective view of the present invention in use.
Figures 7A, 7B, 7C, 7D, 7E, 7F, 7G, 7H, 7I, 7J, 7K, 7L:
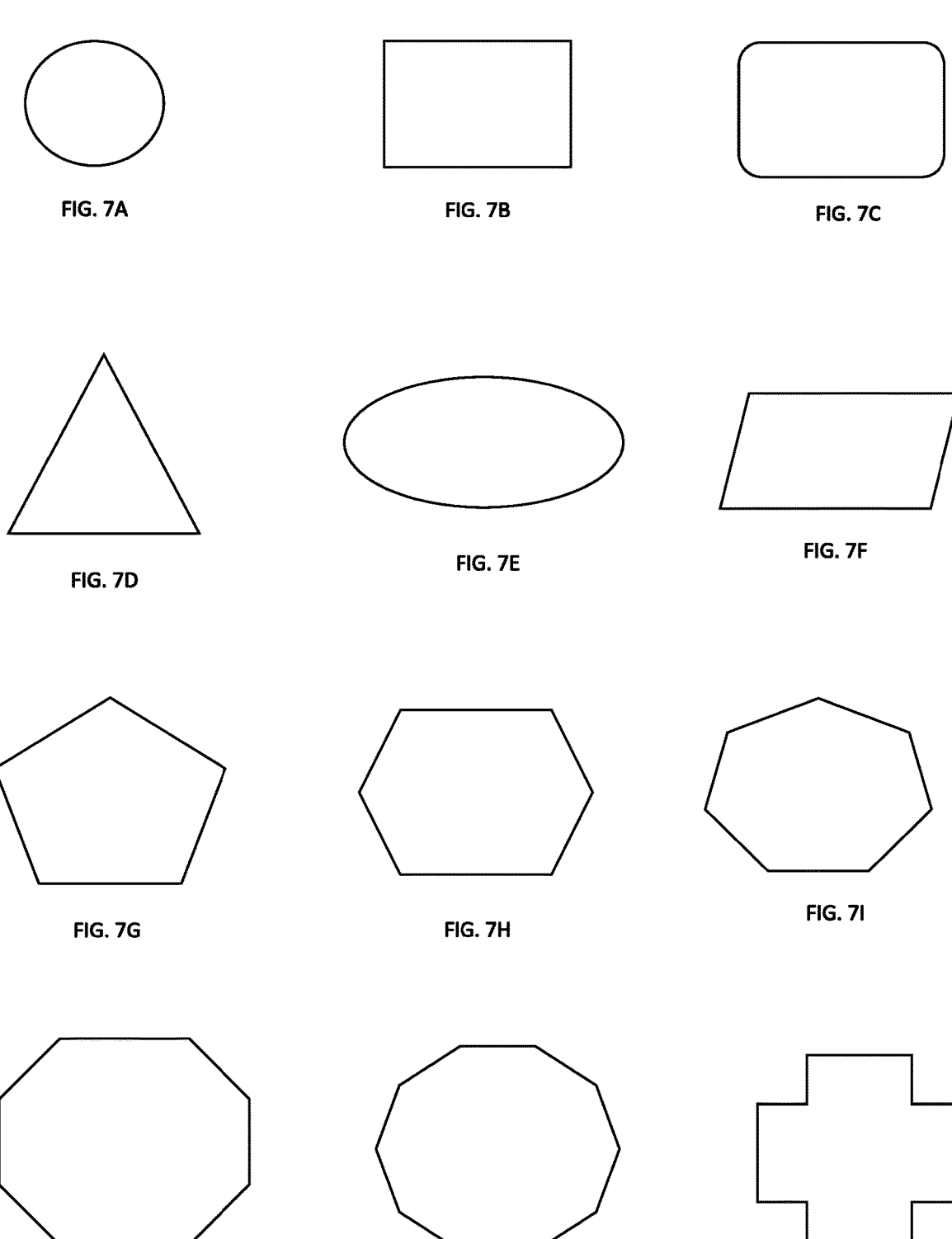
FIGS. 7A-7L illustrate various shapes of the base.

With reference to FIGS. 1A and 5, the present invention is shown for testing a user's ability to balance an object on an apex 5. One embodiment of the invention is comprised of an object having a substantially pyramidal assembly 10 and/or shape. The pyramidal assembly 10 further includes a base 10*c*, a middle section member 10*b* and an apex member 10*a*, where the apex member 10*a* can be made of metallic material in various embodiments. The material of the apex member is metallic since it is durable but can be comprised of any material, preferably durable material.

In various embodiments, the pyramidal assembly 10 can be made of a metallic material. The material of the pyramidal assembly is metallic since it is durable but can be comprised of any material, preferably durable material.

The material is metallic since it is durable but can be comprised of any material in various embodiments.

Figure 8:
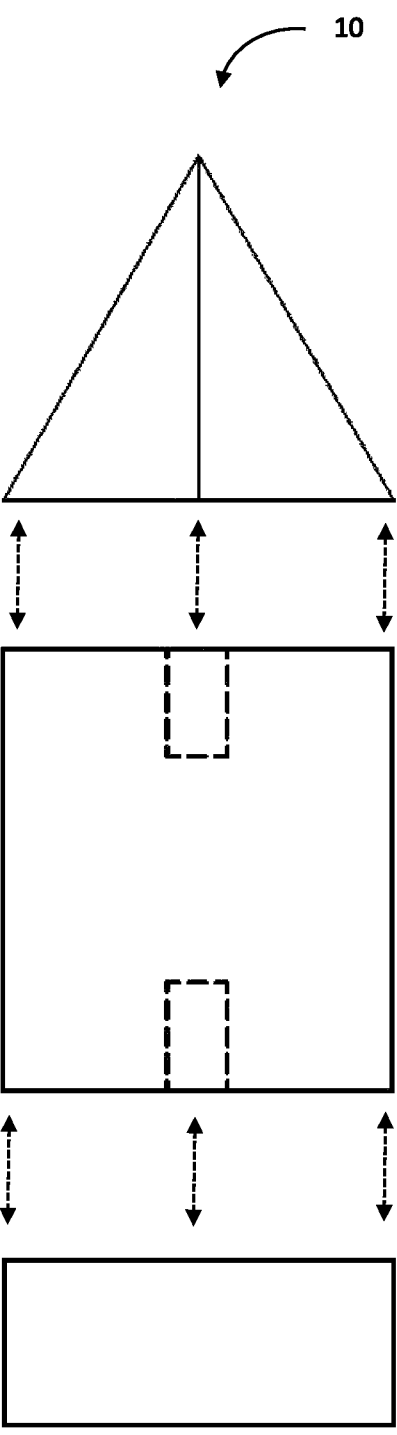
FIG. 8 shows the pyramidal assembly (apex member, middle section member, and base) can be assembled/dissembled via tight interference fit.

In further embodiments, the apex member 10*a*, middle section member 10*b*, and base 10*c* are removable (See FIG. 8). In another embodiment, the apex member 10*a*, middle section member 10*b*, and base 10*c* are coupled by a tight interference fit (See FIG. 8).

In use, the tight interference fit is configured to allow the pyramidal assembly 10 to be assembled and disassembled among its component parts (the apex member 10*a*, middle section member 10*b*, and base 10*c*) by hand, without the need of tools (See FIG. 8).

Figure 1B:
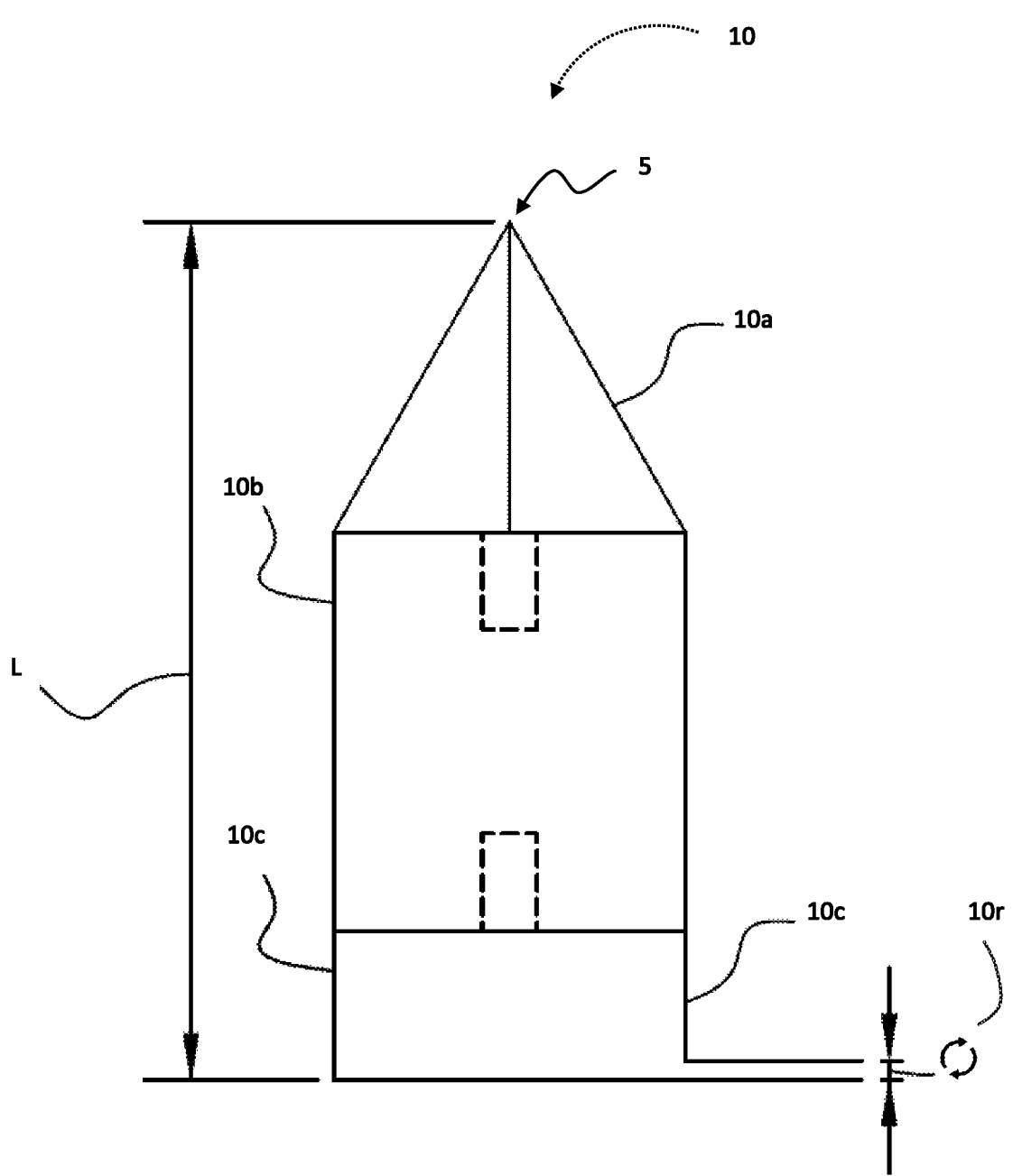
FIG. 1B is another front perspective view of the present invention which includes various dimensions for various embodiments.

In various embodiments, the pyramidal assembly 10 has a height and/or length L. The height and/or length of the pyramidal assembly 10 is 85.5 mm as shown in FIG. 1B.

Figure 2A:
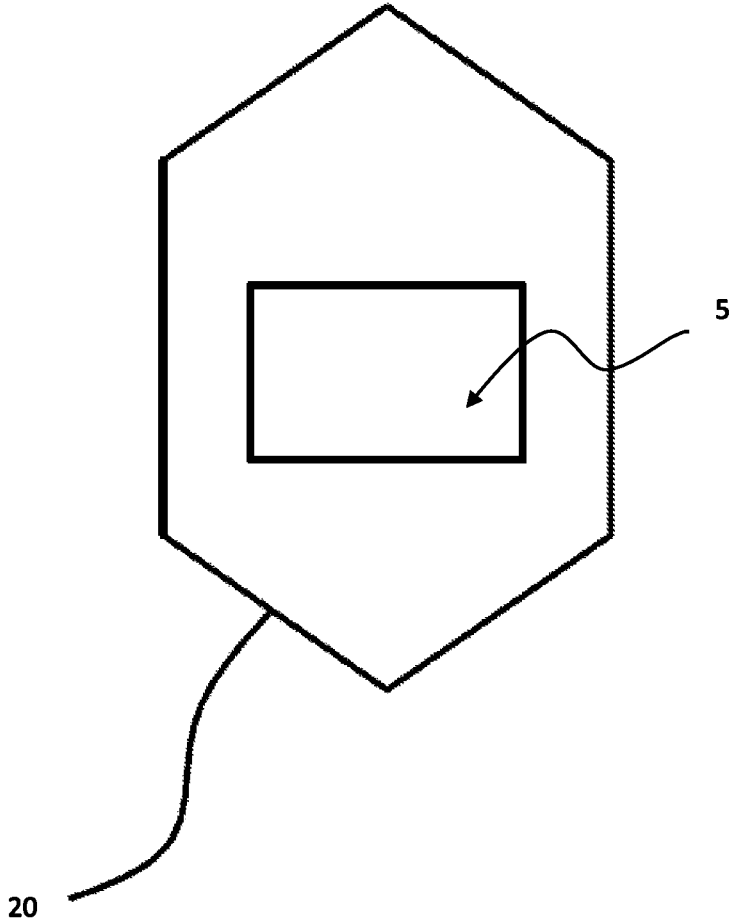
FIG. 2A shows a top view of the present invention.

FIG. 2A illustrates a top view 20 of the pyramidal assembly 10 showing a view of the apex 5 of the present invention.

Figure 2B:
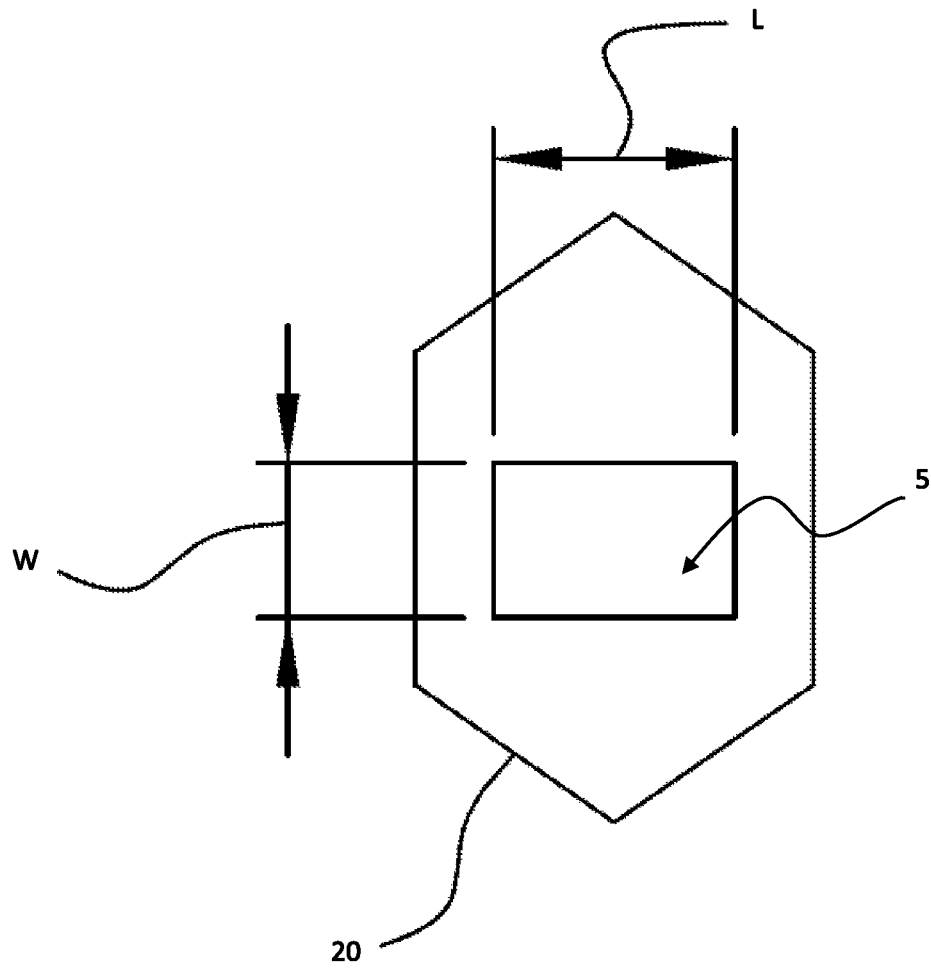
FIG. 2B shows another top view of the present invention which includes various dimensions for various embodiments.

FIG. 2B depicts another top view 20 of the pyramidal assembly 10 showing a view of the apex 5. In various embodiments, the apex 5 has a length of 1.5 mm and a width of 0.8 mm.

Figure 3A:
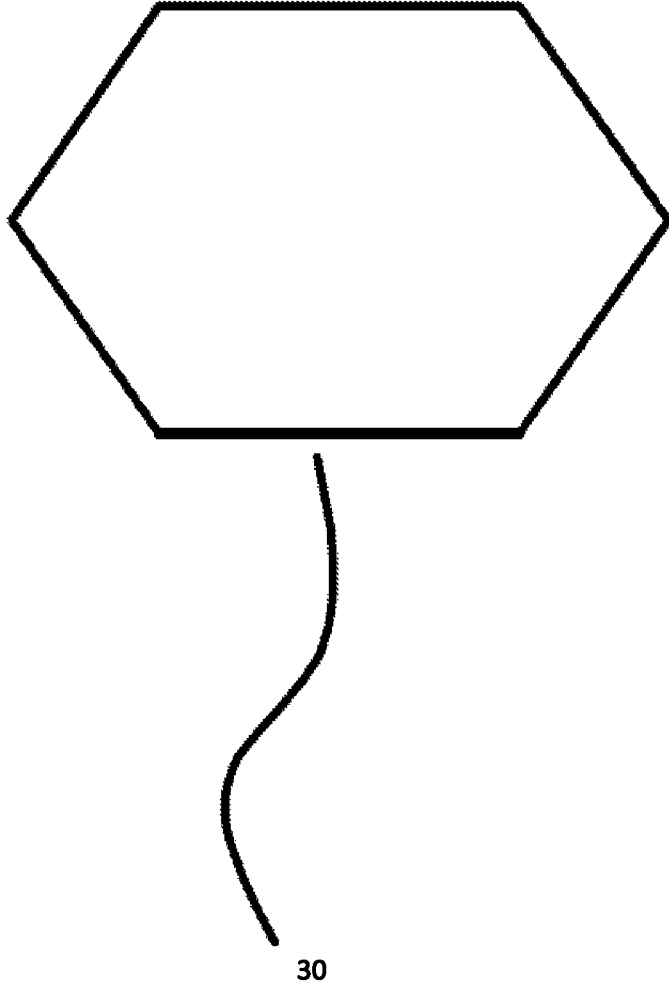
FIG. 3A shows a bottom view of the base.
Figure 3B:
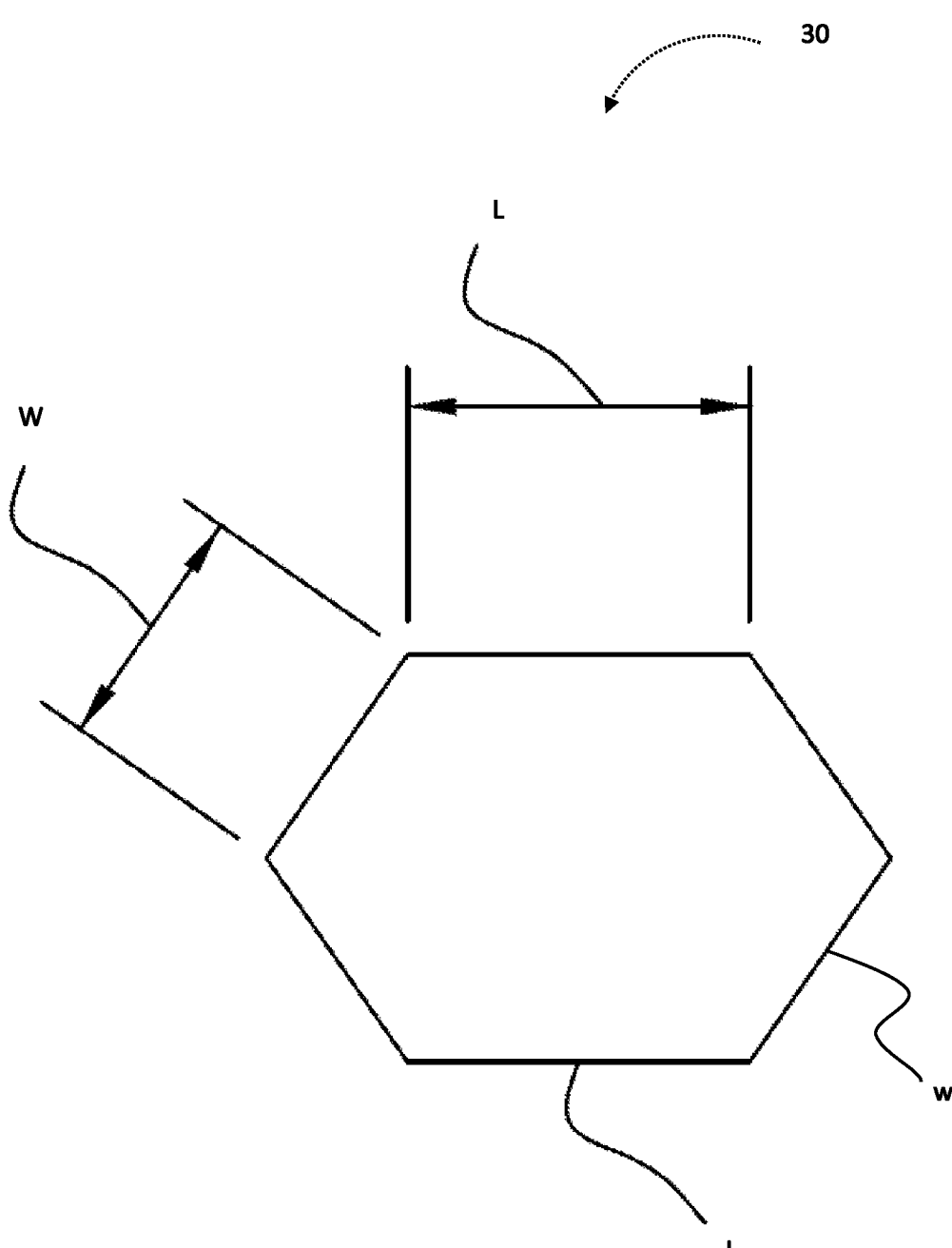
FIG. 3B shows a bottom view of the base which includes various dimensions for various embodiments.

FIG. 3A shows a view of the base 30. In various embodiments, the lengths of the base are 16 mm and the widths of the base are 11.6 mm as shown in FIG. 3B.

Referring to FIGS. 3A and 7A-7L, the shape of the base 30 is selected from various shapes that could be comprised of a triangle, rectangle, square, circle, oval, hexagon, pentagon, heptagon, octagon, decagon, dodecagon, cross, etc.

Figure 4A:
FIG. 4A shows a perspective view of a lever.
Figure 4B:
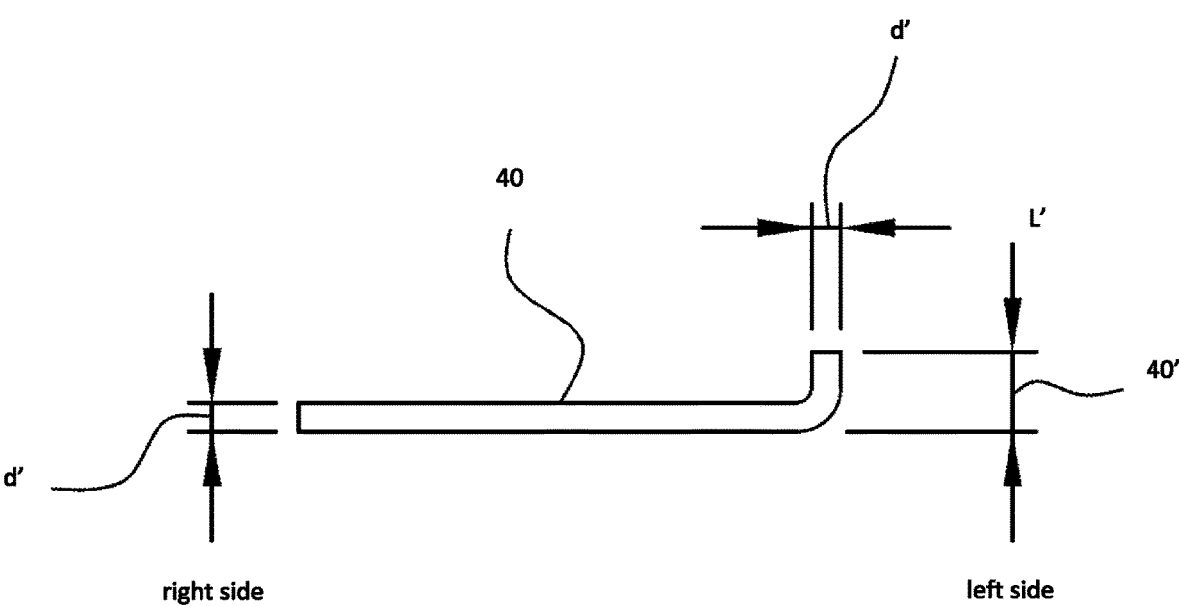
FIG. 4B shows a perspective view of a lever which includes various dimensions for various embodiments.

FIGS. 4A and 4B show side views of a lever 40.

Referring to FIG. 4A, you will see that another embodiment of the invention is comprised of the lever 40 having a length, a weight, and a tapered notch 40' coupled perpendicular to an end thereon, where the tapered notch 40' has a length and weight.

In various embodiments, the depth d' of the lever is 1.1 mm as illustrated in FIG. 4B. In another embodiment, the length L' of the tapered notch 40' is 3 mm (See FIG. 4B). In further embodiments, the weight of the lever is 4 grams.

Figure 4C:
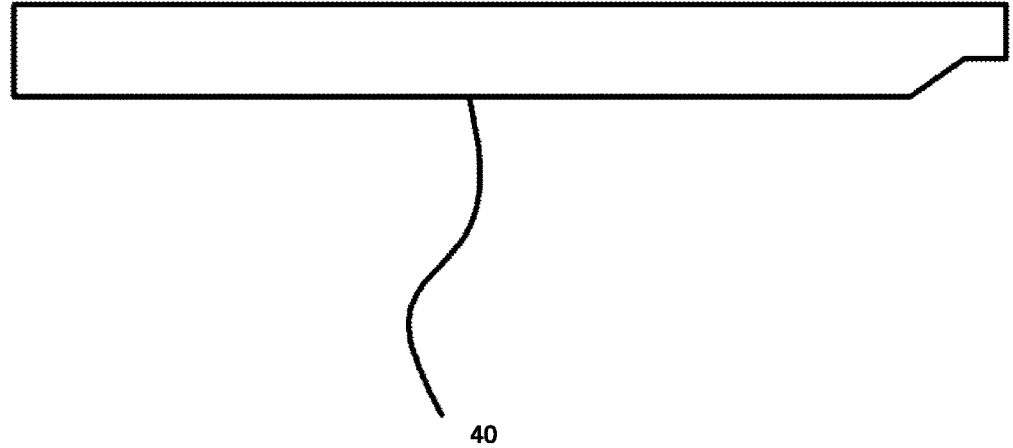
FIG. 4C shows a top view of a lever.
Figure 4D:
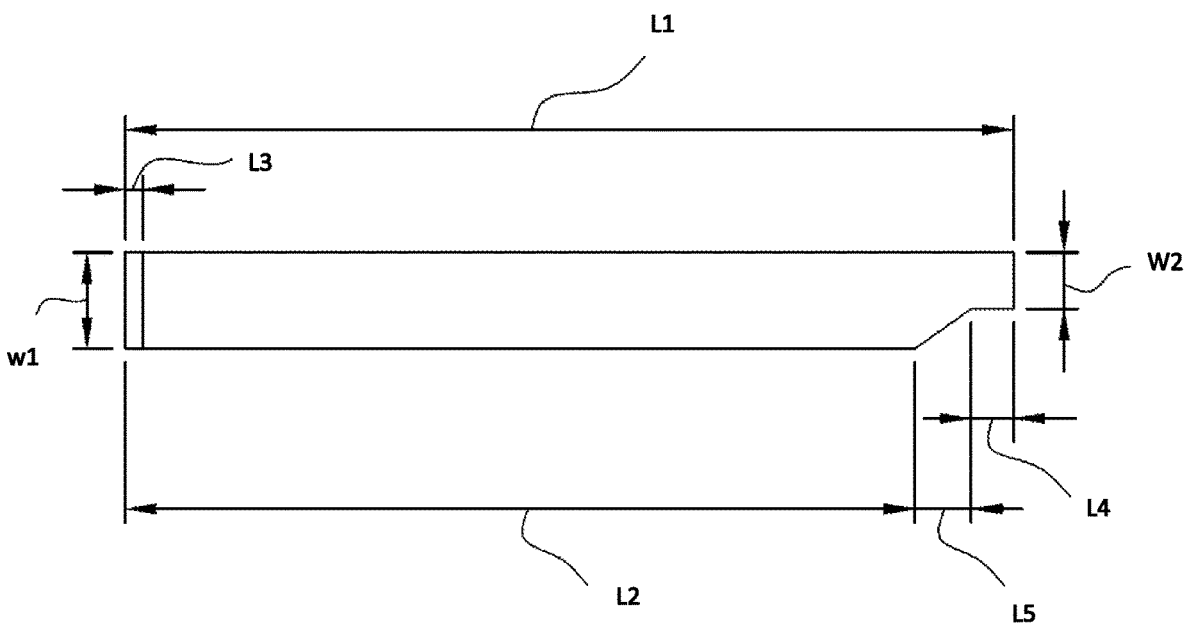
FIG. 4D shows a top view of a lever which includes various dimensions for various embodiments.

FIGS. 4C and 4D show top views of the lever 40.

In various embodiments, the total approximate length L1 of the lever 40 is approximately 76.3 mm as illustrated in FIG. 4D. In another embodiment, the approximate length L2 of the lever base is 66.8 mm. In an additional embodiment of the present invention, the approximate length of the bottom notch L3 is 1.1 mm. In a further embodiment, the approximate length of the tapered notched L4 and L5 (40') is 6.2 mm and 3.7 mm respectively. In one embodiment, the width w2 of the tapered notch is 3.7 mm. In another embodiment of the present invention, the width w1 of the bottom notch L3 is 6.3 mm.

Optionally, the tapered notch 40' can be coupled to only one end of the lever 40 as shown in FIG. 4A or tapered notches can be coupled to both ends of the lever. Further, a tapered notch 40' can be coupled to various positions on the lever 40, or a tapered notch 40' can be configured to be slidably adjustable on the lever 40 for adding a further challenge to users when trying to balance the lever 40 on the apex 5 in the shortest amount of time.

In use, a user places the lever 40 on a top section of the apex 5, where the lever is rockably coupled to the apex until securely/firmly balanced thereon as shown in FIG. 5. In a further embodiment of the present invention, when testing a user's ability and skill to balance the lever on the apex, it can be optionally performed under a timed condition.

In use, a user can also rotate 10r the base 10c after the lever 40 is balanced on the apex 5 as shown in FIG. 5 to further test a user's patience, coordination, concentration, and critical thinking skills. When rotating 10r the base 10c, the objective will be for the user to rotate 10r the base 10c without knocking the lever 40 off the apex 5 in the balanced position. In use, this embodiment of the present invention can optionally be performed under a timed condition.

Referring to FIG. 6, execution diagram 600 shows the process for testing a user's ability to balance a lever on an apex. Starting at block 610, the method includes the step of providing an object to a user having a substantially pyramidal shape, the pyramidal shape further having a base and an apex; at 620, providing the user with a lever, the lever having a length, a weight, and a tapered notch coupled perpendicular to an end thereon, wherein the tapered notch has a length and weight; at 630, allowing the user to place the lever on a top section of the apex, the apex made of metallic material; optionally at 640, timing the user's ability and skill to balance the lever on the apex; and optionally at 650, allowing the user to rotate the base after the lever has been balanced on the apex to further test a user's patience, coordination, concentration, and critical thinking skills. When rotating the base, the objective will be for the user to rotate the base without knocking the lever off the apex in the balanced position. In use, this embodiment of the present invention can optionally be performed under a timed condition.

It should be understood that the foregoing relates to various embodiments of the invention and modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

INDUSTRIAL APPLICABILITY

The invention pertains to a balancing toy, game, or tool for improving the patience, coordination, concentration, and critical thinking skills of a user, which may be of value or importance to various industries such as the retail, game, entertainment, and education industries.

What is claimed is:

1. A method of testing a user's ability to balance a lever on an apex, the method comprising the steps of:

providing an object to a user, the object having a substantially pyramidal shape;

providing the user with a lever, the lever having a length, a weight, and a tapered notch coupled perpendicular to an end thereon, wherein the tapered notch having a length and weight;

allowing the user to place the lever on a top section of an apex;

timing the user's skill to balance the lever on the apex; and allowing allowing the user to rotate the base after the lever has been balanced on the apex to further test a user's patience, coordination, concentration, and critical thinking skills.

2. The method of claim 1, wherein the object is comprised of a base, a middle section member, and the apex member.

3. The method of claim 2, wherein the apex member, middle section member, and base are removable.

4. The method of claim 2, wherein the apex member, middle section member, and base are coupled by a tight interference fit.

5. The method of claim 1 further comprising the step of providing an object having a pyramidal assembly, the pyramidal assembly forming component parts comprising the apex member, a middle section member, and a base, wherein the assembly is coupled by a tight interference fit.

6. The method of claim 5 further comprising the step of allowing the pyramidal assembly to be assembled and disassembled among the component parts by the user's hand via the tight interference fit, without the need of tools.

7. The method of claim 5, wherein the tight interference fit allows the pyramidal assembly to be assembled and disassembled among the component parts by the user's hand, without the need of tools.

8. The method of claim 1, wherein the apex member is comprised of metallic material.

9. The method of claim 1, wherein the object is comprised of metallic material.

10. A method of testing a user's ability to balance a lever on an apex, the method comprising the steps of:

providing an object to a user, the object having a pyramidal assembly, the pyramidal assembly forming component parts comprising an apex member, a middle section member, and a base, wherein the pyramidal assembly is coupled by a tight interference fit that allows the pyramidal assembly to be assembled and disassembled among the component parts by the user's hand, without the need of tools;

providing the user with a lever, the lever having a length, a weight, and a tapered notch coupled perpendicular to an end thereon, wherein the tapered notch having a length and weight;

allowing the user to place the lever on a top section of an apex; and timing the user's skill to balance the lever on the apex.

11. The method of claim 10, wherein a shape of the base is selected from the group consisting of a triangle, rectangle, square, circle, oval, hexagon, pentagon, heptagon, octagon, decagon, dodecagon, and cross.

12. The method of claim 10, wherein the apex is made of metallic material.

13. The method of claim 10, wherein the lever further includes a tapered notch coupled perpendicular to an end thereon, and wherein the tapered notch has a length and weight.

14. The method of claim 10, wherein the object is comprised of metallic material.

\* \* \* \* \*